(12) United States Patent
Humphreys et al.

(10) Patent No.: US 7,875,077 B2
(45) Date of Patent: Jan. 25, 2011

(54) SUPPORT STRUCTURE DEVICE AND METHOD

(75) Inventors: Steven C. Humphreys, Chattanooga, TN (US); Scott D. Hodges, Ooltewah, TN (US); Lukas G. Eisermann, Memphis, TN (US); Marc M. Peterman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 856 days.

(21) Appl. No.: 11/031,700

(22) Filed: Jan. 7, 2005

(65) Prior Publication Data

US 2005/0154464 A1 Jul. 14, 2005

Related U.S. Application Data

(60) Provisional application No. 60/534,960, filed on Jan. 9, 2004.

(51) Int. Cl.
*A61F 2/44* (2006.01)
(52) U.S. Cl. .................... 623/17.14; 623/17.15
(58) Field of Classification Search ... 623/17.11–17.16; 606/61, 246–248, 279
See application file for complete search history.

(56) References Cited

U.S. PATENT DOCUMENTS

| | | | |
|---|---|---|---|
| 4,349,921 A | 9/1982 | Kuntz | |
| 4,697,582 A | 10/1987 | Williams | |
| 4,702,930 A * | 10/1987 | Heide et al. | 427/2.27 |
| 4,759,769 A | 7/1988 | Hedman et al. | |
| 4,932,975 A * | 6/1990 | Main et al. | 623/17.12 |
| 5,092,866 A | 3/1992 | Breard et al. | |
| 5,258,031 A * | 11/1993 | Salib et al. | 623/17.15 |
| 5,282,863 A | 2/1994 | Burton | |
| 5,387,213 A | 2/1995 | Breard et al. | |
| 5,401,269 A | 3/1995 | Buttner-Janz et al. | |
| 5,415,661 A | 5/1995 | Holmes | |
| 5,443,515 A | 8/1995 | Cohen et al. | |
| 5,458,864 A | 10/1995 | Tsugeno et al. | |
| 5,507,816 A | 4/1996 | Bullivant | |
| 5,554,194 A | 9/1996 | Sanders | |

(Continued)

FOREIGN PATENT DOCUMENTS

DE 101 35771 A1 2/2003

(Continued)

OTHER PUBLICATIONS

U.S. Appl. No. 11/342,961, filed Jan. 30, 2006, Yu, et al.

(Continued)

*Primary Examiner*—Thomas C Barrett
*Assistant Examiner*—Andrew Yang

(57) ABSTRACT

An artificial vertebral joint is interposed between a superior vertebra and an inferior vertebra. The artificial vertebral joint comprises a rostral joint component having a first surface adapted for engagement with an endplate of the superior vertebra, a first anterior articulation surface, and a support tab adapted for extending from the first surface and for engaging a portion of the endplate. The portion of the endplate extends from the first surface to a posterior edge of the endplate. The joint further comprises a caudal joint component having a second surface adapted for engagement with an endplate of the inferior vertebra and a spacer component adapted for interposition between the rostral joint component and the caudal joint component.

23 Claims, 8 Drawing Sheets

U.S. PATENT DOCUMENTS

| | | | |
|---|---|---|---|
| 5,556,431 A | 9/1996 | Buttner-Janz | |
| 5,562,660 A | 10/1996 | Grob | |
| 5,562,737 A | 10/1996 | Graf | |
| 5,562,738 A | 10/1996 | Boyd et al. | |
| 5,672,175 A | 9/1997 | Martin | |
| 5,674,296 A | 10/1997 | Bryan et al. | |
| 5,676,701 A | 10/1997 | Yuan et al. | |
| 5,702,450 A * | 12/1997 | Bisserie | 623/17.16 |
| 5,895,428 A | 4/1999 | Berry | |
| 5,899,941 A | 5/1999 | Nishijima et al. | |
| RE36,221 E | 6/1999 | Breard et al. | |
| 5,928,284 A | 7/1999 | Mehdizadeh | |
| 5,961,516 A | 10/1999 | Graf | |
| 6,019,792 A | 2/2000 | Cauthen | |
| 6,039,763 A | 3/2000 | Shelokov | |
| RE36,758 E | 6/2000 | Fitz | |
| 6,106,557 A | 8/2000 | Robioneck et al. | |
| 6,113,637 A | 9/2000 | Gill | |
| 6,132,464 A | 10/2000 | Martin | |
| 6,146,421 A * | 11/2000 | Gordon et al. | 623/17.15 |
| 6,156,067 A | 12/2000 | Bryan et al. | |
| 6,159,211 A | 12/2000 | Boriani et al. | |
| 6,179,874 B1 | 1/2001 | Cauthen | |
| 6,179,875 B1 | 1/2001 | Strempel | |
| 6,228,118 B1 | 5/2001 | Gordon | |
| 6,231,609 B1 | 5/2001 | Mehdizadeh | |
| 6,238,396 B1 | 5/2001 | Lombardo | |
| 6,325,827 B1 * | 12/2001 | Lin | 623/17.16 |
| 6,368,350 B1 | 4/2002 | Erickson et al. | |
| 6,387,130 B1 | 5/2002 | Stone et al. | |
| 6,402,750 B1 | 6/2002 | Atkinson et al. | |
| 6,419,703 B1 | 7/2002 | Fallin et al. | |
| 6,517,580 B1 | 2/2003 | Ramadan et al. | |
| 6,527,804 B1 | 3/2003 | Gauchet et al. | |
| 6,540,747 B1 | 4/2003 | Marino | |
| 6,540,785 B1 * | 4/2003 | Gill et al. | 623/17.14 |
| 6,565,571 B1 | 5/2003 | Jackowski et al. | |
| 6,565,605 B2 | 5/2003 | Goble et al. | |
| 6,572,653 B1 * | 6/2003 | Simonson | 623/17.13 |
| 6,579,319 B2 | 6/2003 | Goble et al. | |
| 6,582,466 B1 | 6/2003 | Gauchet | |
| 6,582,468 B1 | 6/2003 | Gauchet | |
| 6,610,091 B1 | 8/2003 | Reiley | |
| 6,610,093 B1 | 8/2003 | Pisharodi | |
| 6,669,729 B2 | 12/2003 | Chin | |
| 6,679,915 B1 | 1/2004 | Cauthen | |
| 6,709,458 B2 | 3/2004 | Michelson | |
| 6,749,635 B1 | 6/2004 | Bryan | |
| 6,811,567 B2 | 11/2004 | Reiley | |
| 6,908,484 B2 | 6/2005 | Zubok et al. | |
| 6,949,123 B2 | 9/2005 | Reiley | |
| 6,994,727 B2 | 2/2006 | Khandkar et al. | |
| 7,052,515 B2 | 5/2006 | Simonson | |
| 7,083,649 B2 * | 8/2006 | Zucherman et al. | 623/17.11 |
| 7,083,650 B2 | 8/2006 | Moskowitz et al. | |
| 7,090,698 B2 | 8/2006 | Goble et al. | |
| 7,291,150 B2 | 11/2007 | Graf | |
| 7,311,732 B2 * | 12/2007 | Link et al. | 623/17.15 |
| 2002/0095154 A1 | 7/2002 | Atkinson et al. | |
| 2002/0123806 A1 | 9/2002 | Reiley | |
| 2002/0133155 A1 | 9/2002 | Ferree | |
| 2002/0151895 A1 | 10/2002 | Soboleski et al. | |
| 2003/0004572 A1 | 1/2003 | Goble et al. | |
| 2003/0009226 A1 * | 1/2003 | Graf | 623/17.16 |
| 2003/0028250 A1 | 2/2003 | Reiley et al. | |
| 2003/0040797 A1 | 2/2003 | Fallin et al. | |
| 2003/0055427 A1 | 3/2003 | Graf | |
| 2003/0139812 A1 | 7/2003 | Garcia et al. | |
| 2003/0139813 A1 | 7/2003 | Messerli et al. | |
| 2003/0191532 A1 | 10/2003 | Goble et al. | |
| 2003/0199981 A1 | 10/2003 | Ferree | |
| 2003/0199982 A1 | 10/2003 | Bryan | |
| 2003/0204259 A1 | 10/2003 | Goble et al. | |
| 2003/0204260 A1 | 10/2003 | Ferree | |
| 2003/0204271 A1 | 10/2003 | Ferree | |
| 2003/0233146 A1 | 12/2003 | Grinberg et al. | |
| 2004/0002761 A1 | 1/2004 | Rogers et al. | |
| 2004/0002762 A1 | 1/2004 | Hawkins | |
| 2004/0006391 A1 | 1/2004 | Reiley | |
| 2004/0024462 A1 | 2/2004 | Ferree et al. | |
| 2004/0030390 A1 | 2/2004 | Ferree | |
| 2004/0030391 A1 | 2/2004 | Ferree | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049279 A1 | 3/2004 | Sevrain | |
| 2004/0049281 A1 | 3/2004 | Reiley | |
| 2004/0138749 A1 | 7/2004 | Zucherman et al. | |
| 2004/0181284 A1 | 9/2004 | Simonson | |
| 2004/0181285 A1 | 9/2004 | Simonson | |
| 2004/0220670 A1 | 11/2004 | Eisermann et al. | |
| 2005/0033439 A1 | 2/2005 | Gordon et al. | |
| 2005/0043800 A1 | 2/2005 | Paul et al. | |
| 2005/0143820 A1 | 6/2005 | Zucherman et al. | |
| 2005/0149196 A1 | 7/2005 | Zucherman et al. | |
| 2005/0154461 A1 | 7/2005 | Humphreys et al. | |
| 2005/0154462 A1 | 7/2005 | Zucherman et al. | |
| 2005/0154464 A1 | 7/2005 | Humphreys et al. | |
| 2005/0154465 A1 | 7/2005 | Hodges et al. | |
| 2005/0154466 A1 | 7/2005 | Humphreys et al. | |
| 2005/0154467 A1 | 7/2005 | Peterman et al. | |
| 2005/0171608 A1 | 8/2005 | Peterman et al. | |
| 2005/0171609 A1 | 8/2005 | Humphreys et al. | |
| 2005/0171610 A1 | 8/2005 | Humphreys et al. | |
| 2005/0192671 A1 | 9/2005 | Bao et al. | |
| 2005/0197702 A1 | 9/2005 | Coppes et al. | |
| 2005/0234551 A1 | 10/2005 | Fallin et al. | |
| 2005/0234555 A1 | 10/2005 | Sutton et al. | |
| 2005/0240270 A1 | 10/2005 | Zubok et al. | |
| 2005/0256578 A1 | 11/2005 | Blatt et al. | |
| 2005/0261773 A1 | 11/2005 | Ferree | |
| 2005/0277930 A1 | 12/2005 | Parsons | |
| 2005/0277938 A1 * | 12/2005 | Parsons | 606/69 |
| 2005/0283237 A1 | 12/2005 | Zucherman et al. | |
| 2006/0004448 A1 * | 1/2006 | Casey | 623/17.11 |
| 2006/0009849 A1 | 1/2006 | Reiley | |
| 2006/0036325 A1 | 2/2006 | Paul et al. | |
| 2006/0069438 A1 | 3/2006 | Zucherman et al. | |
| 2006/0069440 A1 | 3/2006 | Zucherman et al. | |
| 2006/0085076 A1 * | 4/2006 | Krishna et al. | 623/17.15 |
| 2006/0089717 A1 | 4/2006 | Krishna et al. | |
| 2006/0178745 A1 | 8/2006 | Bartish, Jr. et al. | |
| 2006/0241769 A1 | 10/2006 | Gordon et al. | |
| 2006/0241771 A1 | 10/2006 | Gordon et al. | |
| 2008/0015693 A1 | 1/2008 | Le Couedic | |

FOREIGN PATENT DOCUMENTS

| | | |
|---|---|---|
| DE | 20 2004 015198 | 11/2004 |
| EP | 0 677 277 A2 | 10/1995 |
| EP | 1 281 361 A1 | 2/2003 |
| FR | 2 676 911 A1 | 12/1992 |
| FR | 2 799 638 | 4/2001 |
| WO | WO 96/00049 | 1/1996 |
| WO | WO 99/53871 | 10/1999 |
| WO | WO 00/04851 | 2/2000 |
| WO | WO 01/39678 | 6/2001 |
| WO | WO 01/45576 | 6/2001 |
| WO | WO 02/47586 | 6/2002 |

| WO | WO 03/041618 A2 | 5/2003 |
| WO | WO 03/045262 A2 | 6/2003 |
| WO | WO 03/084449 | 10/2003 |
| WO | WO 03/101350 | 12/2003 |
| WO | WO 2004/034935 | 4/2004 |
| WO | WO 2004/041131 | 5/2004 |
| WO | WO 2004/098465 | 11/2004 |
| WO | WO 2005/112835 | 12/2005 |
| WO | 20080015696 | 1/2008 |

OTHER PUBLICATIONS

U.S. Appl. No. 11/343,159, filed Jan. 30, 2006, Braddock, Jr. et al.
U.S. Appl. No. 11/393,488, filed Mar. 30, 2006, Yu, et al.
U.S. Appl. No. 11/494,311, filed Jul. 27, 2006, Yu, et al.
Patent Cooperation Treaty—European Patent Office, "Notification of Transmittal of the International Search Report and the Written Opinion of the Internatinal Searching Authority, or the Declaration," International Application No. PCT/US2005/000704, Aug. 23, 2005, 7 pages.
Patent Cooperation Treaty—European Patent Office, "Notification of Transmittal of the International Search Report and the Written Opinion of the International Searching Authority, or the Declaration," International Application No. PCT/US2005/000656, Aug. 23, 2005, 8 pages.
Patent Cooperation Treaty—European Patent Office, "Notification of Transmittal of the International Search Report and the Written Opinion of the Intematinal Searching Authority, or the Declaration," International Application No. PCT/US2005/000648, Jun. 6, 2005, 6 pages.
Patent Cooperation Treaty—European Patent Office, "Notification of Transmittal of the International Search Report and the Written Opinion of the International Searching Authority, or the Declaration," International Application No. PCT/US2005/000705, Jun. 6, 2005, 7 pages.
Patent Cooperation Treaty—European Patent Office, "Invitation to Pay Additional Fees/Communication Relating to the Results of the Partial International Search," International Application No. PCT/US2005/000586, Jun. 8, 2005, 5 pages.
Patent Cooperation Treaty—European Patent Office, "Notification of Transmittal of the International Search Report and the Written Opinion of the Internatinal Searching Authority, or the Declaration," International Application No. PCT/US2005/000585, Jun. 8, 2005, 6 pages.

* cited by examiner

SUPPORT STRUCTURE DEVICE AND METHOD

CROSS-REFERENCE

This application claims priority from U.S. Provisional Patent Application Ser. No. 60/534,960 filed on Jan. 9, 2004, entitled "Posterior Lumbar Arthroplasty." The following applications also claim priority to the above referenced provisional application and are related to the present application. They are incorporated by reference herein.
- U.S. Utility patent application Ser. No. 11/031,602, filed on Jan. 7, 2005 and entitled "Spinal Arthroplasty Device and Method;"
- U.S. Utility patent application Ser. No. 11/031,603, filed on Jan. 7, 2005 and entitled "Dual Articulating Spinal Device and Method;"
- U.S. Utility patent application Ser. No. 11/031,780, filed on Jan. 7, 2005 and entitled "Split Spinal Device and Method;"
- U.S. Utility patent application Ser. No. 11/031,904, filed on Jan. 7, 2005 and entitled "Interconnected Spinal Device and Method;"
- U.S. Utility patent application Ser. No. 11/031,783, filed on Jan. 7, 2005 and entitled "Mobile Bearing Spinal Device and Method;"
- U.S. Utility patent application Ser. No. 11/031,781, filed on Jan. 7, 2005 and entitled "Centrally Articulating Spinal Device and Method;" and
- U.S. Utility patent application Ser. No. 11/031,903, filed on Jan. 7, 2005 and entitled "Posterior Spinal Device and Method."

TECHNICAL FIELD

Embodiments of the invention relate generally to devices and methods for accomplishing spinal surgery, and more particularly in some embodiments, to spinal arthroplasty devices capable of being placed posteriorally into the vertebral disc space. Various implementations of the invention are envisioned, including use in total spine arthroplasty replacing, via a posterior approach, both the disc and facet functions of a natural spinal joint.

BACKGROUND

As is known the art, in the human anatomy, the spine is a generally flexible column that can take tensile and compressive loads, allows bending motion and provides a place of attachment for ribs, muscles and ligaments. Generally, the spine is divided into three sections: the cervical, the thoracic and the lumbar spine. FIG. 1 illustrates schematically the lumbar spinal 1 and the sacrum regions 3 of a healthy, human spinal column. The sections of the spine are made up of individual bones called vertebrae and the vertebrae are separated by intervertebral discs which are situated therebetween.

FIG. 2 illustrates a portion of the right side of a lumbar spinal region with a healthy intervertebral disc 5 disposed between two adjacent vertebrae 7, 9. In any given joint, the top vertebra may be referred to as the superior vertebra and the bottom one as the inferior vertebra. Each vertebra comprises a generally cylindrical body 7a, 9a, which is the primary area of weight bearing, and three bony processes, e.g., 7b, 7c, 7d (two of which are visible in FIG. 2). As shown in FIG. 7A, in which all of the processes are visible, processes 7b, 7c, 7d extend outwardly from vertebrae body 7 at circumferentially spaced locations. The processes, among other functions, provide areas for muscle and ligament attachment. Neighboring vertebrae may move relative to each other via facet components 7e (FIG. 2), which extend from the cylindrical body of the vertebrae and are adapted to slide one over the other during bending to guide movement of the spine. There are two facet joints, each defined by upper and lower facet components, associated with adjacent vertebra. A healthy intervertebral disc is shown in FIG. 3. As shown in FIG. 3, an intervertebral disc has 4 regions: a nucleus pulposus 11, a transition zone 13, an inner annulus fibrosis region 15 and an outer annulus fibrosis 17. Generally, the inner annulus fibrosis region 15 and the outer annulus fibrosis region 17 are made up of layers of a fibrous gristly material firmly attached to the vertebral bodies above and below it. The nucleus pulposus 11 is typically more hydrated in nature.

These intervertebral discs function as shock absorbers and as joints. They are designed to absorb the compressive and tensile loads to which the spinal column may be subjected while at the same time allowing adjacent vertebral bodies to move relative to each other a limited amount, particularly during bending (flexure) of the spine. Thus, the intervertebral discs are under constant muscular and/or gravitational pressure and generally are the first parts of the lumbar spine to show signs of "wear and tear".

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

One surgical procedure for treating these conditions is spinal arthrodesis (i.e., spine fusion), which has been performed both anteriorally and/or posteriorally. The posterior procedures include in-situ fusion, posterior lateral instrumented fusion, transforaminal lumbar interbody fusion ("TLIF") and posterior lumbar interbody fusion ("PLIF"). Solidly fusing a spinal segment to eliminate any motion at that level may alleviate the immediate symptoms, but for some patients maintaining motion may be advantageous. It is also known to surgically replace a degenerative disc or facet joint with an artificial disc or an artificial facet joint, respectively. However, none of the known devices or methods provide the advantages of the embodiments of the present disclosure.

Accordingly, the foregoing shows there is a need for an improved spinal arthroplasty that avoids the drawbacks and disadvantages of the known implants and surgical techniques.

SUMMARY

In one embodiment, an artificial vertebral joint is interposed between a superior vertebra and an inferior vertebra. The artificial vertebral joint comprises a rostral joint component having a first surface adapted for engagement with an endplate of the superior vertebra, a first anterior articulation surface, and a support tab adapted for extending from the first surface and for engaging a portion of the endplate. The portion of the endplate extends from the first surface to a posterior edge of the endplate. The joint further comprises a caudal joint component having a second surface adapted for engagement with an endplate of the inferior vertebra and a spacer component adapted for interposition between the rostral joint component and the caudal joint component.

In a second embodiment, a method of implanting an artificial spinal device between superior and inferior vertebrae comprises creating a first exposure to access an intervertebral space between the superior and inferior vertebrae and inserting at least a portion of the artificial spinal device through the first exposure. The method further comprises engaging a rostral component of the artificial spinal device with an inferior endplate of the superior vertebra, positioning a support tab to extend posteriorly from the rostral component, and engaging the support tab with at least a portion of the inferior endplate. The portion of the inferior endplate extends from the rostral component to a posterior edge of the endplate. The method further comprises engaging a caudal component of the artificial spinal device with a superior endplate of the inferior vertebra.

In a third embodiment, an artificial spinal joint creates a portion of a coupling between a superior vertebra and an inferior vertebra. The joint comprises an anterior joint replacement component and a bridge coupled to the anterior joint replacement and extending posteriorly from the anterior joint replacement beyond one or both generally cylindrical body portions of the superior and inferior vertebrae. The joint further comprises a posterior joint replacement component coupled to the bridge and a support tab coupled to the anterior joint replacement component and engaging a posterior surface of the generally cylindrical body portion of the superior vertebra.

The embodiments disclosed may be useful for degenerative changes of the lumbar spine, post-traumatic, discogenic, facet pain or spondylolisthesis, and/or to maintain motion or generate fusion in multiple levels of the lumbar spine.

Additional and alternative features, advantages, uses and embodiments are set forth in or will be apparent from the following description, drawings, and claims.

DESCRIPTION

The drawings illustrate various embodiments of an artificial intervertebral joint for replacing an intervertebral disc or the combination of an intervertebral disc and at least one corresponding facet joint. Various embodiments of the artificial intervertebral joint according to the principles of the disclosure may be used for treating any of the problems that lend themselves to joint replacement including particularly, for example, degenerative changes of the lumbar spine, post-traumatic, discogenic, facet pain or spondylolisthesis and/or to maintain motion in multiple levels of the lumbar spine.

Figure 1:
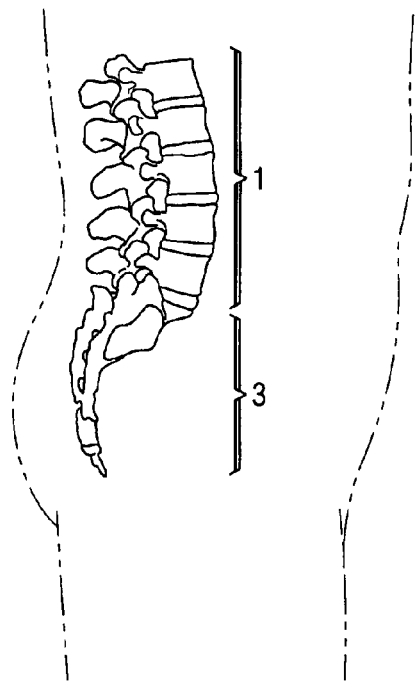
FIG. 1 is a side elevation schematic view of the lumbar spinal and the sacrum regions of a healthy, human spinal column.
Figure 2:
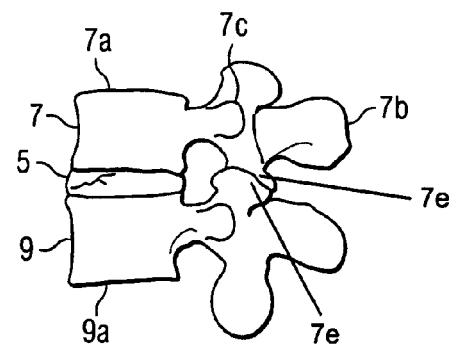
FIG. 2 is a detailed perspective view showing a portion of the right side of the lumbar vertebrae shown in FIG. 1 with a healthy disc disposed between two vertebrae.
Figure 3:
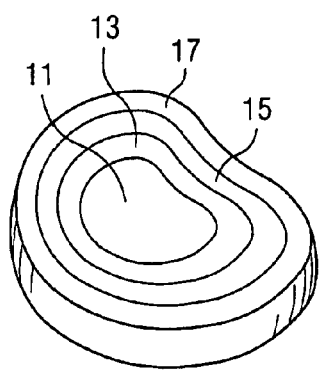
FIG. 3 is a top perspective view of the intervertebral disc shown in FIG. 2 illustrating the major portions of the disc.
Figure 4:
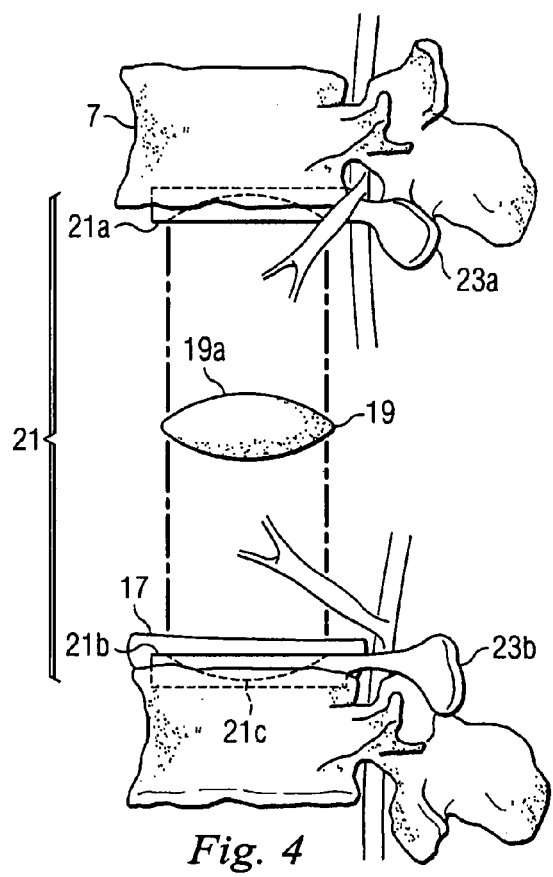
FIG. 4 is a side exploded elevation view of a portion of a lumbar spine showing a first embodiment of an artificial intervertebral joint constructed according to the principles of the disclosure.
Figure 5:
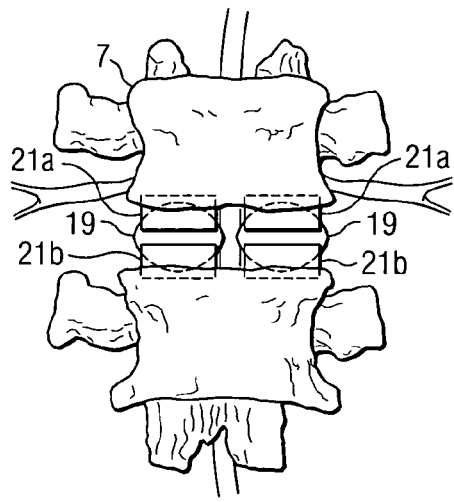
FIG. 5 is an anterior elevation view of a portion of a lumbar spine showing the superior, disc and inferior portions of the left and right halves of an assembled artificial intervertebral joint constructed according to the first embodiment of the disclosure.

FIGS. 4-7 illustrate a first exemplary embodiment of an artificial intervertebral joint. As illustrated in FIGS. 4 and 5, each joint is composed of two arthroplasty halves, each of which has a spacer or disc 19 and a retaining portion 21. The retaining portion 21 includes a first retaining portion 21a and a second retaining portion 21b. In the example illustrated in FIG. 4, the first retaining portion 21a is superior to (above) the second retaining portion 21b and the disc 19 is situated therebetween. Although the artificial intervertebral joint according to this exemplary embodiment has two halves for each of the first retaining portion and the second retaining portion, it should be understood that alternative embodiments may be implemented such that the artificial intervertebral joint has a single first retaining member, a single second retaining member and a single spacer. It should also be understood that alternative embodiments may also be carried out with arthroplasties having a first retaining portion, a second retaining portion, and/or a disc which each consist of unequal sized halves or more than two components.

Further, as illustrated in FIG. 4, the first retaining portion 21a and the second retaining portion 21b are situated between two adjacent vertebrae. More particularly, the first retaining portion may be situated along an inferior surface of the upper of the two adjacent vertebrae and the second retaining portion may be situated above a superior surface of the lower of the two adjacent vertebrae. However, it should be understood by one of ordinary skill in the art that the first retaining portion and second retaining portion are not limited to such an arrangement, and may be oriented in different positions and/or shaped differently than what is illustrated herein.

The surfaces of the retaining portions 21a, 21b of the arthroplasty that contact the remaining end plates of the vertebrae may be coated with a beaded material or plasma sprayed to promote bony ingrowth and a firm connection therebetween. In particular, the surface to promote bone ingrowth may be a cobalt chromium molybdenum alloy with a titanium/calcium/phosphate double coating, a mesh surface, or any other effective surface finish. Alternatively or in combination, an adhesive or cement such as polymethylmethacrylate (PMMA) may be used to fix all or a portion of the implants to one or both of the endplates.

As discussed in more detail below, a significant portion of the outer annulus region 17 (see, e.g., FIGS. 4, 7B), in some embodiments about 300 degrees, may be retained on the inferior portion of the end plate, which acts as a stop retaining the lower retaining portions in place until bone ingrowth occurs to firmly attach the retaining portions to their respective vertebrae (FIG. 4 only shows a portion of the outer annulus 17 that is retained). In contrast, in conventional anterior arthroplasty about 270 degrees of the outer annulus region 17 typically is removed. In addition, pedicle screws may also be used for immediate fixation as described in more detail in connection with other embodiments discussed below.

In the various embodiments of this disclosure, the first retaining portion 21a and the second retaining portion 21b are structured so as to retain the disc 19 therebetween. For example, in the case of a disc 19 with two convex surfaces 19a, each of the first retaining portion 21a and the second retaining portion 21b may have a concave surface 21c which defines a space within which the disc 19 may be retained. For example, in the exemplary embodiment shown in FIG. 4, the upper convex surface 19a of the disc 19 fits within the concavity defined by the concave surface 21c of the first retaining portion 21a and the lower convex surface 19b of the disc 19 fits within the concavity defined by the concave surface 21c of the second retaining portion 21b.

Figure 6:
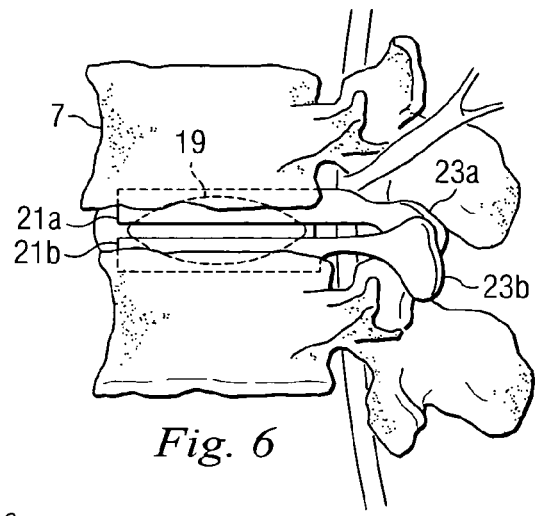
FIG. 6 is a side elevation view of the right half of the artificial intervertebral joint shown in FIG. 5.

FIG. 5 illustrates an anterior view of an exemplary assembled artificial intervertebral joint with both arthroplasty halves in place, and FIG. 6 shows a side view of the assembled artificial intervertebral joint shown in FIG. 5. As illustrated in FIGS. 5 and 6, the disc 19 is retained between the first retaining portion 21a and the second retaining portion 21b. It should be understood that although the disc 19 may be held between the first retaining portion 21a and the second retaining portion 21b, the disc 19 is free to slidably move within the space defined by the corresponding surfaces 21a of the first retaining portion 21a and the second retaining portion 21b. In this manner, limited movement between the adjacent vertebrae is provided.

In the exemplary embodiment illustrated in FIGS. 4, 5 and 6, the disc 19 is a separate component which is inserted between the first retaining portion 21a and the second retaining portion 21b. However, as discussed below, it should be understood that the spacer or disc 19 may be integrally formed with or integrated into in one or both of the first retaining portion 21a and the second retaining portion 21b.

Figure 7A:
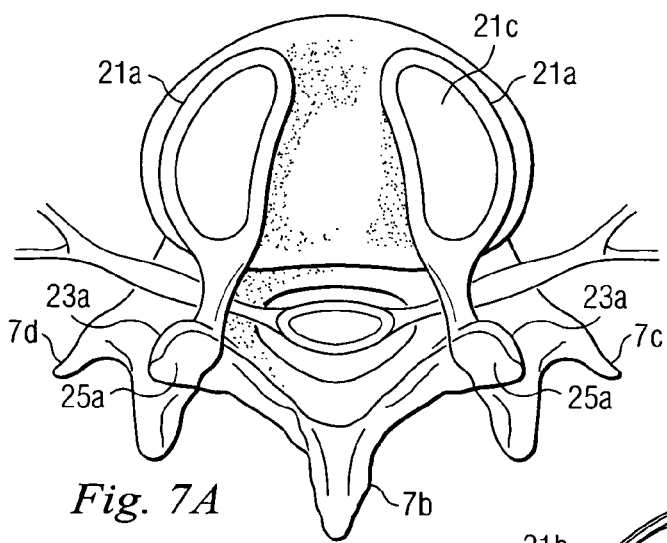
FIG. 7A is a transverse, bottom-up-view of a portion of a lumbar spine showing the superior portion of the artificial intervertebral joint illustrated in FIG. 4.
Figure 7B:
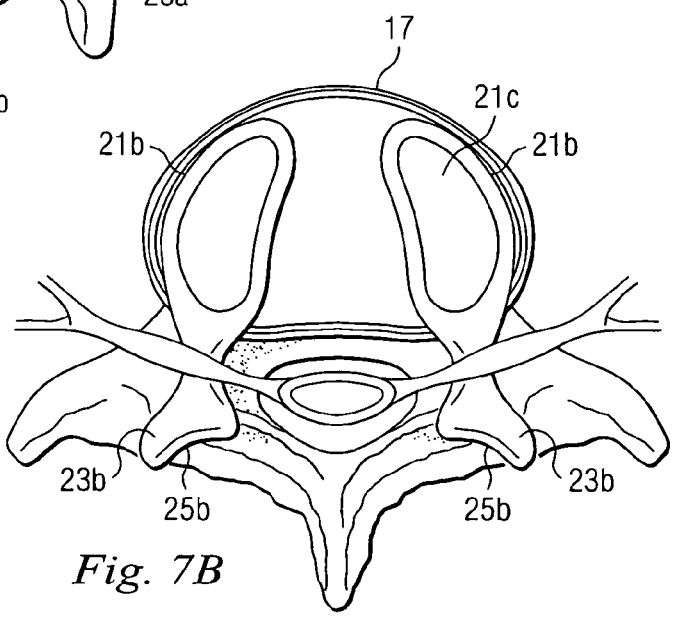
FIG. 7B is a transverse, top-down-view of a portion of a lumbar spine showing the inferior portion of the artificial intervertebral joint illustrated in FIG. 4.
Figure 8:
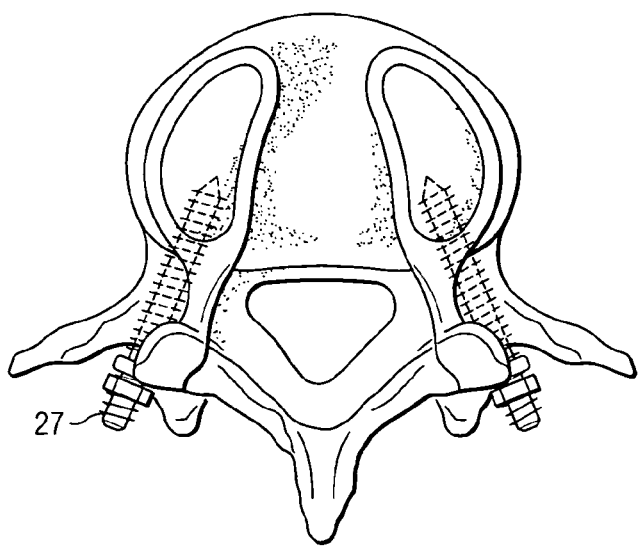
FIG. 8 is a transverse, bottom-up-view of a portion of a lumbar spine showing a second embodiment of a superior portion of an artificial intervertebral joint in which pedicle screws are used to assist in implantation.
Figure 9:
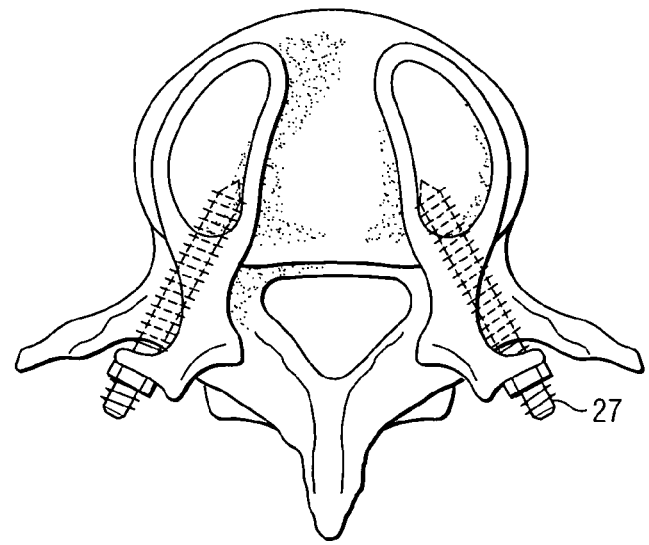
FIG. 9 is a transverse, top-down-view of a portion of a lumbar spine showing a second embodiment of an inferior portion of an artificial intervertebral joint in which pedicle screws are used to assist in implantation.
Figure 10:
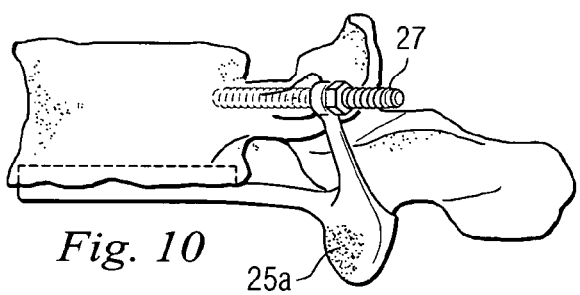
FIG. 10 is a lateral view of a portion of a lumbar spine showing the superior portion of the artificial intervertebral joint shown in FIG. 8 with one of the pedicle screws being visible.
Figure 11:
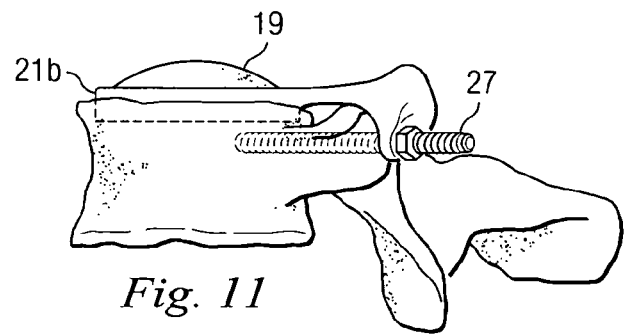
FIG. 11 is a lateral view of a portion of a lumbar spine showing the inferior and integrated disc portions of an artificial integral intervertebral joint shown in FIG. 9 with one of the pedicle screws being visible.
Figure 12:
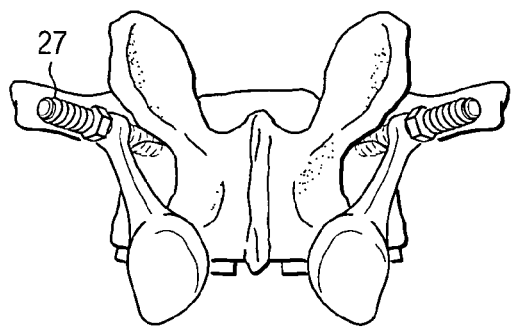
FIG. 12 is a posterior view of a portion of a lumbar spine showing the superior portion of the artificial intervertebral joint shown in FIG. 8 with two pedicle screws being visible.
Figure 13:
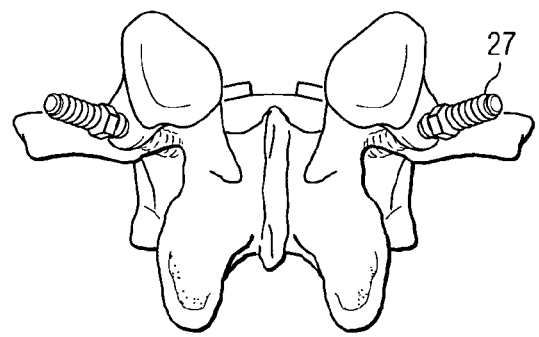
FIG. 13 is a posterior view of a portion of a lumbar spine showing the inferior portion of the artificial intervertebral joint shown in FIG. 9 with two pedicle screws being visible.
Figure 14:
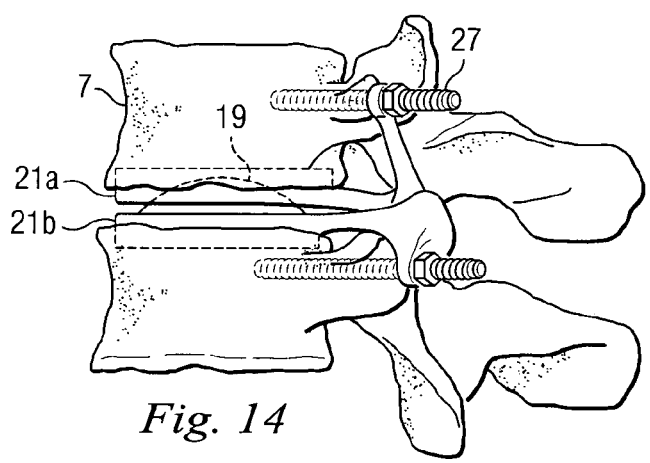
FIG. 14 is a side elevation view of a portion of a lumbar spine showing the second embodiment with pedicle screws in an assembled position.

In the exemplary embodiment of the disclosure, as illustrated best in FIGS. 4, 6, 7A and 7B, each of the retaining portions of the artificial intervertebral joint includes a first artificial facet component 23a and a second artificial facet component 23b. As shown in FIGS. 7A and 7B, the first artificial facet component 23a has a face 25a and the corresponding second artificial facet component 23b has a face 25b configured such that the face 25a matingly fits with the face 25b to stabilize adjacent vertebrae while preserving and guiding the mobility of each vertebrae with respect to the other vertebrae. Each set of the upper and lower retaining portions 21a, 21b may have a pair of facet components 23a, 23b, which together define a facet joint. For a total joint replacement with facets according to this embodiment, the left and right arthroplasties would define two adjacent facet joints when viewed from the posterior.

Regardless of whether artificial facet joints are provided, the respective upper and lower retaining portions associated with the left and right halves of the arthroplasty may be completely independent from the other. That is, as shown in FIG. 7A, for example, the first retaining portions 21a associated with each half are not in direct contact with each other. The same is true with respect to the second retaining portions 21b shown in FIG. 7B. However, it should be understood by one of ordinary skill in the art that, even in the embodiment of the disclosure which includes artificial facet joints, at least a portion of the first retaining portions 21a of each half and/or at least a portion of the second retaining portions 21b of each half may directly contact and/or be connected to each other as described in more detail in connection with the discussion of FIGS. 17-18.

Further, in the various embodiments of the disclosure, the disc 19, the first retaining portion 21a and the second retaining portion 21b may be made of any appropriate material which will facilitate a connection that transmits compressive and tensile forces while providing for the aforementioned slidable motion in a generally transverse direction between each of the adjacent surfaces. For example, in the first embodiment, the first retaining portion 21a and the second retaining portion 21b may be typically made from any metal or metal alloy suitable for surgical implants such as stainless steel, titanium, and cobalt chromium, or composite materials such as carbon fiber, or a plastic material such as polyetheretherketone (PEEK) or any other suitable materials. The disc may be made from plastic such as high molecular weight polyethylene or PEEK, or from ceramics, metal, and natural or synthetic fibers such as, but not limited to, carbon fiber, rubber, or other suitable materials. Generally, to help maintain the sliding characteristic of the surfaces, the surfaces may be polished and/or coated to provide smooth surfaces. For example, if the surfaces are made of metal, the metal surfaces may be polished metal.

FIGS. 8-14 illustrate a second embodiment of an artificial intervertebral joint. Only features that differ from the first embodiment are discussed in detail herein. In the second exemplary embodiment, securing components, such as, for example, pedicle screws 27 are provided to provide a more secure and immediate connection between each of the first retaining portion 21a and/or the second retaining portion 21b to the corresponding vertebra. In addition, this embodiment illustrates a disc 19 which is integrated with one of the retaining portions, here lower retaining portion 21b. Disc 19 may be integrally formed from the same material as its retaining portion, but also may be separately formed from similar or dissimilar materials and permanently connected thereto to form an integral unit. In this embodiment, the disc 19 and the retaining portions may be all formed from metal.

Figure 15:
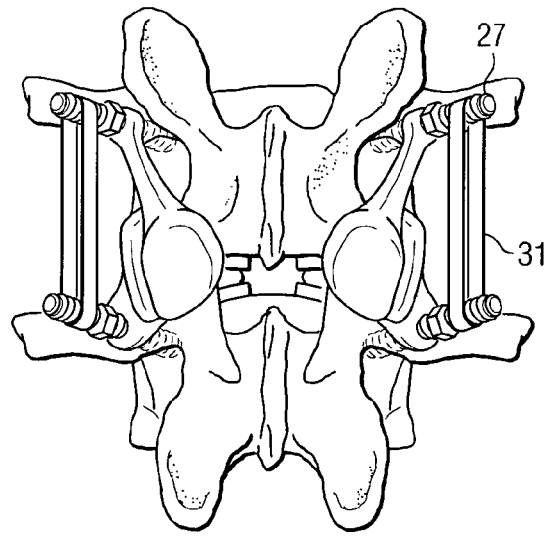
FIG. 15 is a posterior view of a portion of a lumbar spine showing a third embodiment of the inferior, disc and superior portions of an artificial intervertebral joint in which tension bands are used.
Figure 16:
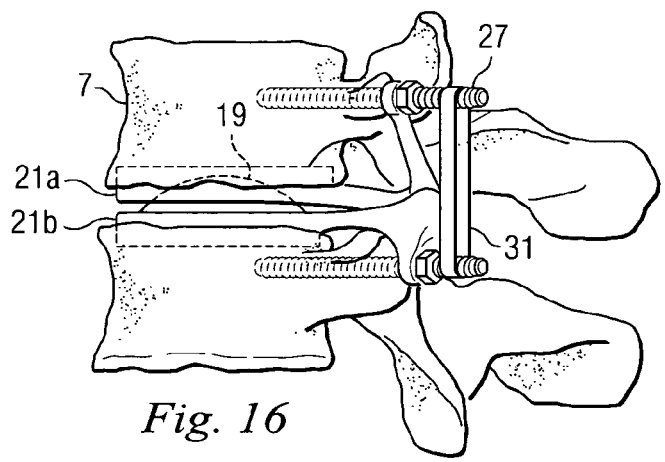
FIG. 16 is a side elevation view of a portion of a lumbar spine showing the third embodiment in which tension bands are used in an assembled position.

FIGS. 15 and 16 illustrate a third embodiment of an artificial intervertebral joint. In the third exemplary embodiment, additional securing components, such as, for example, tension bands 31 are provided to supplement or replace the function of posterior ligaments that limit the mobility between adjacent vertebrae by securing the first retaining portion 21a to the second retaining portion 21b. As shown in FIGS. 15-16, posterior tension bands 31 may be provided by wrapping them around the corresponding pedicle screws 27 or other convenient attachment points.

Figure 17:
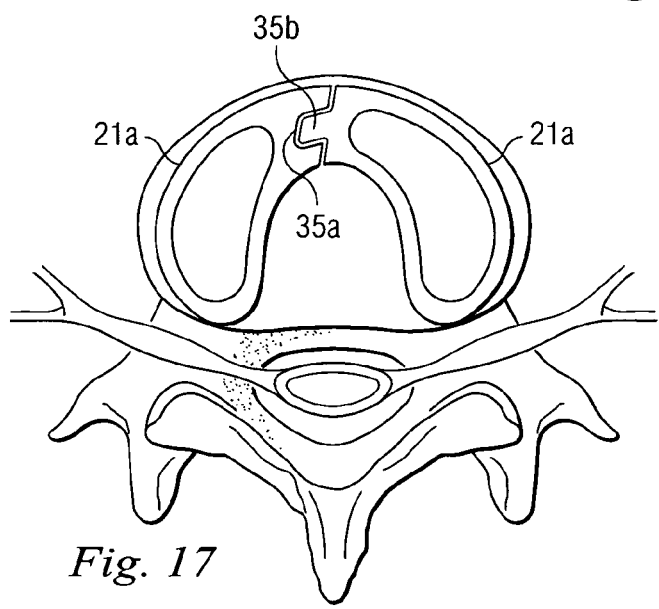
FIG. 17 is a transverse, bottom-up-view of a portion of a lumbar spine showing the superior portion of a fourth embodiment of an artificial intervertebral joint constructed according to the principles of the disclosure in which the facet joints are not replaced.
Figure 18:
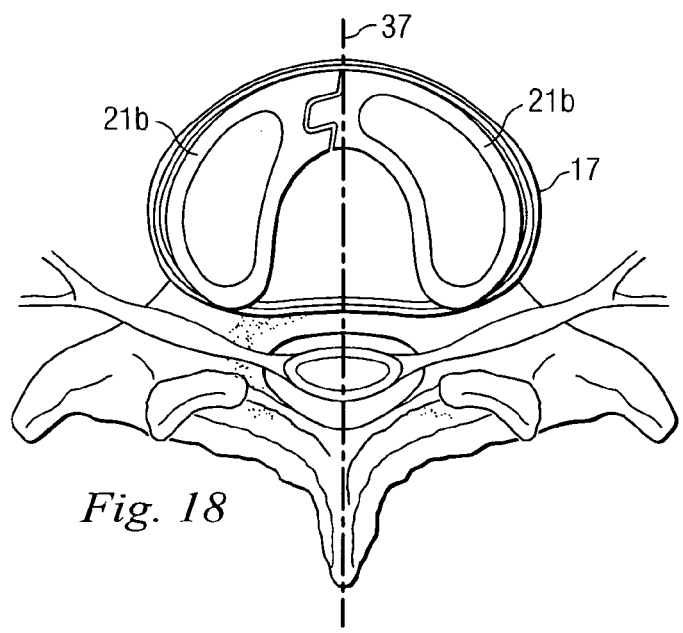
FIG. 18 is a transverse, top-down-view of a portion of a lumbar spine showing the inferior portion of the fourth embodiment of an artificial intervertebral joint.

FIGS. 17 and 18 illustrate a fourth embodiment of an artificial intervertebral joint. In the exemplary embodiment illustrated in FIGS. 17 and 18, the artificial intervertebral joint may have all of the features discussed above except for artificial facet components. In this embodiment, the natural facet joints remain. The ligamentous tension band may also be left intact in some embodiments. In addition, this embodiment includes a specific example of an anterior midline connection between respective upper and lower retaining portions, which assists in maintaining the placement of the first retaining portion 21a and the second retaining portion 21b.

FIGS. 17 and 18 illustrate that it is possible to provide a first retaining portion 21a with a lock and key type pattern which is complemented by the corresponding mating portion provided on the second retaining portion 21b. More particularly, one half of the first retaining portion 21a has an outer boundary with a U-shaped portion 35a while the other half of the corresponding first retaining portion 21a has an outer boundary with a protruding portion 35b, which fits into the U-shaped portion 35a. As a result, each half of the first retaining portion 21a, 21b may be maintained in a predetermined position. However, the upper or lower retaining portions may fit together and/or be connected in the interbody space, e.g., near their midline anterior portions, in any manner that facilitates implantation and/or assists in providing and/or retaining the joint in a generally stable, symmetrical configuration. It may be even more important to provide such connection between the lower retaining portions due to the inward forces provided by annulus 17 remaining on the inferior end plate as shown in FIG. 18. A midline connection between the respective lower retaining portions will resist the force of the outer annulus tending to cause migration of the retaining portions toward the midline 37.

As shown in the various exemplary embodiments, other than the portions of the first and/or second retaining portions which may fit together like a lock and key to maintain the placement of the portions relative to each other, each half of the artificial intervertebral joint may be generally symmetrical about the midline 37 of the vertebrae.

Again, these exemplary embodiments are merely illustrative and are not meant to be an exhaustive list of all possible designs, implementations, modifications, and uses of the invention. Moreover, features described in connection with one embodiment of the disclosure may be used in conjunction with other embodiments, even if not explicitly stated above.

While it should be readily apparent to a skilled artisan from the discussion above, a brief description of a suitable surgical procedure that may be used to implant the artificial joint is provided below. Generally, as discussed above, the artificial intervertebral joint may be implanted into a body using a posterior transforaminal approach similar to the known TLIF or PLIF procedures. According to this approach, an incision, such as a midline incision, may be made in the patient's back and some or all of the affected disc and surrounding tissue may be removed via the foramina. Depending on whether any of the facet joints are being replaced, the natural facet joints may be trimmed to make room for the artificial facet joints. Then, the halves of the artificial intervertebral joint may be inserted piecewise through the left and right transforaminal openings, respectively. That is, the pieces of the artificial intervertebral joint including the upper and lower retaining portions, with or without facet components, and the artificial disc, if provided separately, fit through the foramina and are placed in the appropriate intervertebral space. The pieces of the artificial joint may be completely separated or two or more of them may be tied or packaged together prior to insertion through the foramina by cloth or other materials known in the art. In cases where at least a portion of the outer annulus of the natural disc can be retained, the lower retaining portions of each side of the artificial intervertebral joint are inserted such that they abut a corresponding portion of the annulus. If a midline anterior connection is provided, the left and right halves of the retaining members are fitted together and held in place by the outer annulus. As such, the remaining portion of the annulus may be in substantially the same place as it was prior to the procedure.

Further, in the cases where the annulus of the natural disc must be removed completely or this is insufficient annulus remaining, it is possible, for example, to use the embodiment of the disclosure where the pedicle screws are implemented so as to be assured that the pieces of the artificial intervertebral joint remain in place. It should be understood by one of ordinary skill in the art that the artificial joint could be implanted via an anterior approach or a combined anterior and posterior approach, although the advantages of a posterior procedure would be limited. For example, some of the pieces of the artificial intervertebral joint may be inserted from an anterior approach and others posteriorly. The anteriorly and posteriorly placed portions could be fitted together similar to the embodiment shown in FIGS. 17 and 18.

Figure 19:
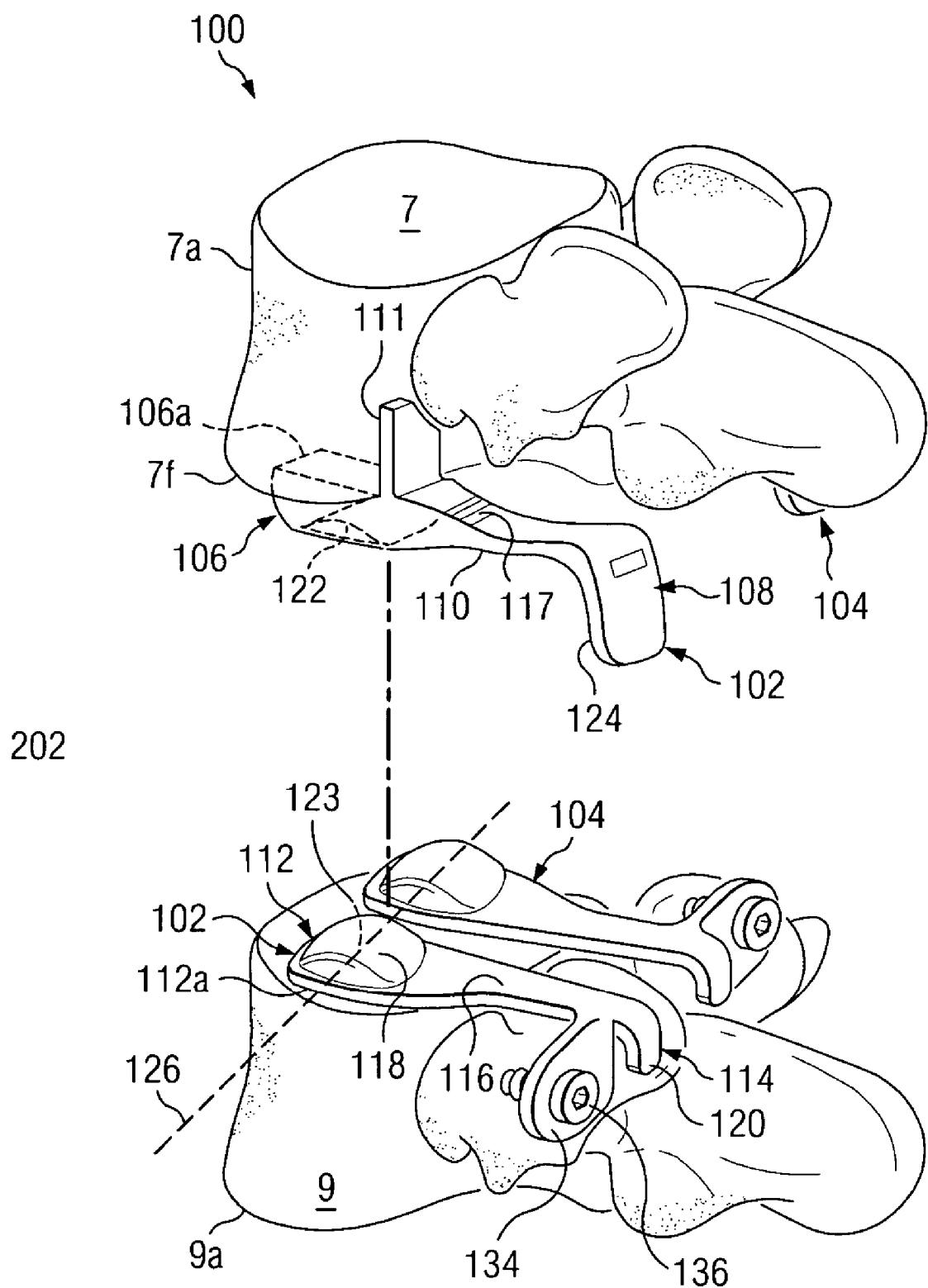
FIG. 19 is an exploded perspective view of another embodiment of the present disclosure.

Referring now to FIG. 19, in this embodiment, an artificial intervertebral joint 100 may include two arthroplasty halves 102, 104 which may be inserted between the vertebrae 7, 9. The arthroplasty half 102 may include a rostral anterior joint component 106, a rostral posterior joint component 108, and a rostral bridge 110 extending between the anterior component 106 and the posterior component 108. The arthroplasty half 102 may also include a support tab 111 extending from the rostral anterior joint component 106. The arthroplasty half 102 may further include a caudal anterior joint component 112, a caudal posterior joint component 114, and a caudal bridge 116 extending between the anterior component 112 and the posterior component 114. The rostral anterior joint component 106 may include a bone contacting surface 106a and the caudal anterior joint component 112 may include a bone contacting surface 112a. The arthroplasty half 104 may be substantially similar in structure and function to the arthroplasty half 102 and therefore will not be described in further detail.

The terms "rostral" and "caudal" are used in some embodiments to describe the position of components of the embodiments. While rostral is typically used in the art to describe positions toward the head and caudal is used to describe positions toward the tail or foot, as used herein, rostral and caudal are used simply as modifiers for the relative locations of components of the illustrated embodiments. For example, rostral components may be on one side of an illustrated joint, and caudal may be on another side of the joint. Components labeled as rostral or caudal to describe an illustrated embodiment are not intended to limit the orientation of a device or application of a method relative to a patient's anatomy, or to limit the scope of claims to any device or method.

In this embodiment, the rostral bridge 110 may include a jog 117 to create an exit portal and an artificial foramen for the exiting nerve root. Either of the bridges 110, 116, but particularly the caudal bridge 116, may be a "super" or artificial pedicle which may supplement or replace a natural pedicle. Also in this embodiment, the caudal anterior joint component 112 may include a curved protrusion 118, and the caudal posterior joint component 114 may include a posterior protrusion 120. The rostral anterior joint component 106 may include an anterior socket 122 configured to receive the curved protrusion 118. A radius of curvature for the curved protrusion 118 may closely match the radius of curvature for the anterior socket 122 to create a highly constrained ball and socket type engagement. In an alternative embodiment, by increasing the radius of curvature for the socket relative to the radius of the curved protrusion, the curved protrusion may be permitted to translate within the socket. The anterior socket 122 may articulate about a center of rotation 123 of the curved protrusion 118.

The rostral posterior joint component 108 may include a posterior socket 124 configured to engage the posterior protrusion 120. A radius of curvature for the posterior protrusion 120 may be smaller than a radius of curvature for the posterior socket 124, thereby permitting motion and limiting binding between the posterior joint components 108, 114. The radii of curvature for the posterior socket 124 and the posterior protrusion 120 may emanate from a common center of rotation for the arthroplasty half 102. In this embodiment, the radius of curvature for the posterior socket 124 is relatively large, and the resulting joint is loosely constrained. In an alternative embodiment, a tight radius of curvature for the posterior protrusion of the caudal posterior component matched with a rostral posterior component having a tight radius of curvature may create a tightly constrained posterior joint.

The size and shape of the anterior components 106, 112 and the bridge components 110, 116 may be limited by the constraints of a posterior surgical approach. For example, the anterior components 106, 112 may be configured to cover a maximum vertebral endplate area to dissipate loads and reduce subsidence while still fitting through the posterior surgical exposure, Kambin's triangle, and other neural elements. To achieve maximum surface coverage, the material of the anterior components 106, 112 may extend anteriorly from the curved protrusion 118 and the anterior socket 122, respectively. The width of the bridge components 110, 116 are also minimized to pass through Kambin's triangle and to co-exist with the neural elements.

The arthroplasty half 102 further includes features for affixing to the vertebrae 7, 9. It is understood, however, that in an alternative embodiment, the fixation features may be eliminated. Arthroplasty half 102 may include a connection component 134 attached to or integrally formed with the caudal posterior joint component 114. The connection component 134 in this embodiment is an aperture adapted to receive a bone fastener such as screw 136. The orientation of the connection component 134 permits the screw 136 to become inserted extrapedicularly such that the screw travels a path angled or skewed away from a central axis defined through a pedicle. Extrapedicular fixation may be any fixation into the pedicle that does not follow a path down a central axis defined generally posterior-anterior through the pedicle. In this embodiment, the screw passes through a lateral wall of the pedicle and may achieve strong cortical fixation. In all embodiments, the screws may be recessed so as not to interfere with articulations, soft tissues, and neural structures.

In an alternative embodiment, a connection component extending from the posterior component 114 may be oriented to permit the screw to become inserted intrapedicularly such that the screw travels a path generally along the central axis through the pedicle. This type of intrapedicular orientation is shown, for example in FIG. 14. In still another alternative embodiment, the posterior connection component may connect to the generally cylindrical body portion 9a. It is understood that in other alternative embodiments, the connection components may extend at a variety of angles, in a variety of directions from the various components of the arthroplasty half. For example, a connection component may extend from the rostral bridge rather than the rostral anterior joint component. In another alternative embodiment, the support tab may include a connection component such as an aperture adapted to receive a bone fastener such as screw. The orientation of this connection component may permit the screw to affix to the cylindrical vertebral body 7a.

As shown in FIG. 19, the rostral components 106, 108, 110, 111 of the arthroplasty half 102 are integrally formed. It is understood that in a modular alternative embodiment, these components may be removably coupled to one another. For example, the rostral anterior joint component may be installed separate from the bridge. After the anterior component is in place, the bridge may be attached to the anterior component by any fastening mechanism known in the art, for example a threaded connection, a bolted connection, or a latched connection. A modular rostral posterior component may then be attached by a similar fastening mechanism to the bridge to complete the rostral portion of the arthroplasty half.

The arthroplasty halves 102, 104 may be formed of any suitable biocompatible material including metals such as cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various components comprising the arthroplasty halves 102, 104 may be formed of different materials thus permitting metal on metal, metal on ceramic, metal on polymer, ceramic on ceramic, ceramic on polymer, or polymer on polymer constructions.

Bone contacting surfaces of the arthroplasty halves 102, 104, including support tab 111, may include features or coatings which enhance the fixation of the implanted prosthesis. For example, the surfaces may be roughened such as by chemical etching, bead-blasting, sanding, grinding, serrating, and/or diamond-cutting. All or a portion of the bone contacting surfaces of the arthroplasty halves 102, 104 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

The artificial intervertebral joint 100 may be installed between the vertebrae 7, 9 as will be described below. Although installation will be described with respect to arthroplasty half 102, it is understood that the arthroplasty half 104 may be installed in a similar manner. Generally, as discussed above, the artificial intervertebral joint 100 may be implanted into a body using a posterior transforaminal approach similar to the known TLIF or PLIF procedures. PLIF approaches are generally more medial and rely on more retraction of the traversing root and dura to access the vertebral interspace. The space between these structures is known as Kambin's triangle. TLIF approaches are typically more oblique, requiring less retraction of the exiting root, and less epidural bleeding with less retraction of the traversing structures. It is also possible to access the interspace using a far lateral approach, above the position of the exiting nerve root and outside of Kambin's triangle. In some instances it is possible to access the interspace via the far lateral without resecting the facets. Furthermore, a direct lateral approach through the psoas is known. This approach avoids the posterior neural elements completely. Embodiments of the current invention are anticipate that could utilize any of these common approaches.

According to at least one of these approaches, an incision, such as a midline incision, may be made in the patient's back and some or all of the affected disc and surrounding tissue may be removed via the foramina. The superior endplate surface of the vertebra 9 may be milled, rasped, or otherwise resected to match the profile of the caudal anterior bone contacting surface 112a, to normalize stress distributions on the superior endplate surface of the vertebra 9, and/or to provide initial fixation prior to bone ingrowth. The preparation of the endplate of vertebra 9 may result in a flattened surface or in surface contours such as pockets, grooves, or other contours that may match corresponding features on the bone contacting surface 112a. The inferior endplate of the vertebra 7 may be similarly prepared to receive the rostral anterior joint component 106 to the extent allowed by the exiting nerve root and the dorsal root ganglia. Depending on whether any of the facet joints are being replaced, the natural facet joints of vertebrae 7, 9 may be trimmed to make room for the posterior components 108, 114.

The halves 102, 104 of the artificial intervertebral joint 100 may then be inserted piecewise through the left and right transforaminal openings, respectively. That is, the pieces of the artificial intervertebral joint 100 including the rostral and caudal anterior joint components 106, 112 respectively fit through the foramina and are placed in the appropriate intervertebral disc space between the generally cylindrical bodies 7a, 9a. The pieces of the artificial joint 100 may be completely separated or two or more of them may be tied or packaged together prior to insertion through the foramina by cloth or other materials known in the art. In cases where at least a portion of the outer annulus of the natural disc can be retained, the caudal anterior joint components of each side of the artificial intervertebral joint are inserted such that they abut a corresponding portion of the annulus.

The anterior socket 122 may be placed into articulating engagement with the curved protrusion 118. The center of rotation 123 of the joint formed by the socket 122 and the protrusion 118 may be located posteriorly of a central axis 126 extending laterally through the intervertebral disc space between vertebrae 7, 9. The bridges 110, 116 may extend posteriorly from the anterior joint components 106, 112 and posteriorly from the intervertebral disc space. The posterior components 108, 114 are positioned posteriorly of the intervertebral disc space to replace or supplement the function of the natural facet joints. The screw 136 may be inserted through the connection component 134 and into adjacent bone such as the pedicle.

The support tab 111 may engage the posterior surface of the generally cylindrical body portion 7a of vertebra 7 to prevent subsidence of the vertebra 7, particularly the posterior portion of an inferior endplate 7f. The support tab 111 may prevent or limit subsidence of the endplate 7f that may otherwise result from even slight repeated movement of the contacting surface 106a against the endplate 7f. The additional surface area provided by the support tab 111 may dissipate forces over a greater surface area of the vertebra 7, and thus posterior subsidence patterns may be reduced. The support tabs may be configured to dodge neural structures, yet provide targeted bearing support on strong bone. The tab 111 may follow the natural contour of the body portion 7a and thus may form an angle other than ninety degrees with the bone contacting surface 106a.

As installed, the anterior ball and socket type joint created by the rostral anterior joint component 106 and the caudal anterior joint component 112 may be relatively stable and self-centering. Both the anterior joint and the posterior joint, created by the rostral posterior joint component 108 and the caudal posterior joint component 114, allow the arthroplasty half 102 to resist shear forces, particularly anterior-posterior forces. Movement of the rostral anterior joint component 106 relative to the caudal anterior joint component 112 may be limited by the displacement of the posterior protrusion 120 within the posterior socket 124. For example, lateral translation of the rostral anterior joint component 106 relative to the caudal anterior joint component 112 may be limited by the posterior joint. Rotational motion about a longitudinal axis defined by the cylindrical bodies 7a, 9a may be limited both by the constraint in the posterior joint and by the combined constraint provided by the two arthroplasty halves 102, 104. Further, the posterior joint may restrict any true lateral bending degree of freedom.

Pure freedom of motion may be limited to flexion-extension motion about an axis defined through the anterior joints of the arthroplasty halves 102, 104. However, under certain conditions, the joint 100 may overcome these design restrictions to permit limited lateral, rotational, and coupled movements. For example, the anterior joint components 106, 112 may become disconnected from each other and experience limited "lift-off," thereby permitting additional degrees of freedom and coupled motions beyond strict flexion-extension motion. The self-centering nature of the anterior joint may encourage reconnection and alignment after lift-off occurs. The limited disconnection of the anterior joint components 106, 112 may be accommodated by the degree of constraint in the posterior joint. For example, relatively loose constraint in the posterior joint permits greater amounts of lift-off. Some degree of constraint in the posterior joint may be useful, however, to encourage reconnection and alignment of the anterior joint.

In general, a simple, anteriorly located ball and socket joint which is tightly constrained with each component having the same or similar radii of curvature may allow flexion-extension, lateral bending, and torsion motions while resisting shear forces and limiting translation. By adding an additional highly constrained ball and socket joint to the posterior components, an additional degree of freedom may be limited, such as torsion. Additional joints may further limit degrees of freedom of motion. If the anterior or posterior joints are permitted to disconnect or disarticulate additional degrees of freedom may be permitted as described above. Changing the shape of or clearance between the ball and socket components will also permit additional degrees of motion.

The robust and forgiving structure of the anterior and posterior joints also permits misalignment and slight inaccuracy in the placement of the arthroplasty halves 102, 104. For example, the self-aligning ball and socket structure of the anterior joint components 106, 112 tolerates a certain amount of misalignment between the components. Thus, the insertion trajectories for the components 106, 112 may be slightly misaligned. The interaction of the posterior protrusion 120 and the posterior socket 124 may also accommodate parallel misalignment and/or anterior-posterior misalignment between the arthroplasty halves 102, 104.

Figure 20:
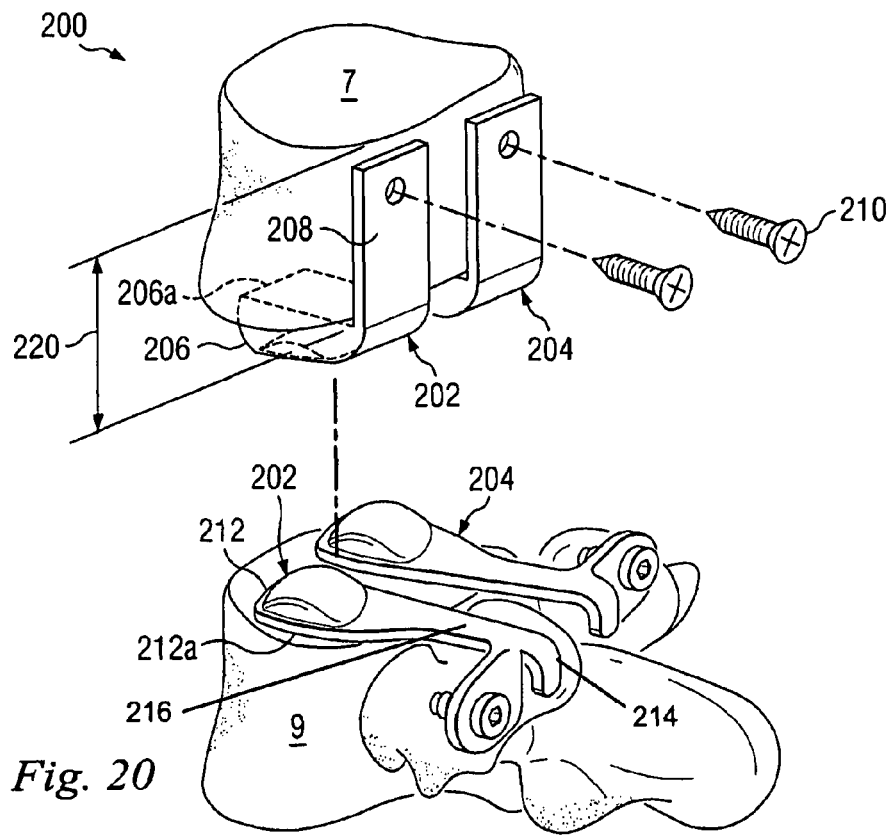
FIG. 20 is an exploded perspective view of another embodiment of the present disclosure.

Referring now to FIG. 20, in this embodiment, an artificial intervertebral joint 200 may include two arthroplasty halves 202, 204 which may be inserted between the vertebrae 7, 9. The artificial intervertebral joint 200 may be substantially similar in structure, installation, and motion to the artificial intervertebral joint 100 except for the differences described. The arthroplasty half 202 may include a rostral anterior joint component 206 and a support tab 208 extending from the rostral anterior joint component 206. A connection component such as a bone screw 210 may extend through the support tab. The arthroplasty half 202 may further include a caudal anterior joint component 212, a caudal posterior component 214, and a caudal bridge 216 extending between the anterior component 212 and the posterior component 214. The rostral anterior joint component 206 may include a bone contacting surface 206*a* and the caudal anterior joint component 212 may include a bone contacting surface 212*a*.

Installation of artificial intervertebral joint 200 between the vertebrae 7, 9, may proceed as described above for artificial intervertebral joint 100 with the following differences. A complete or partial laminectomy may be performed on vertebra 7. The support tab 208 may engage the natural or resected posterior surface of the generally cylindrical body portion 7*a* of vertebra 7 to prevent subsidence of the vertebra 7, particularly the posterior portion of an inferior endplate 7*f*. The additional surface area provided by the support tab 208 may dissipate forces over a greater surface area of the vertebra 7 and thus posterior subsidence patterns may be reduced or eliminated during the course of using the joint 200. The support tab 208 may extend more than half of the height 220 of the body portion 7*a*. In alternative embodiments the support tabs may span any desired height including the entire height 220. The support tabs may be configured to dodge neural structures yet provide targeted bearing support on strong bone. The tab 208 may follow the natural or resected contour of the body portion 7*a* and thus may form an angle other than ninety degrees with the bone contacting surface 106*a*. The tab 208 may be attached to the body portion 7*a* with the connection component which in this embodiment includes inserting the bone screw 210 through the tab 208 and into the vertebra 7. In an alternative embodiment, a plurality of screws may be used to attach the tab to the vertebra. In this embodiment, the rostral posterior joint component is eliminated, however in an alternative embodiment, a rostral anterior joint component similar to component 108 may be included to provide the constraint of a posterior joint.

Figure 21:
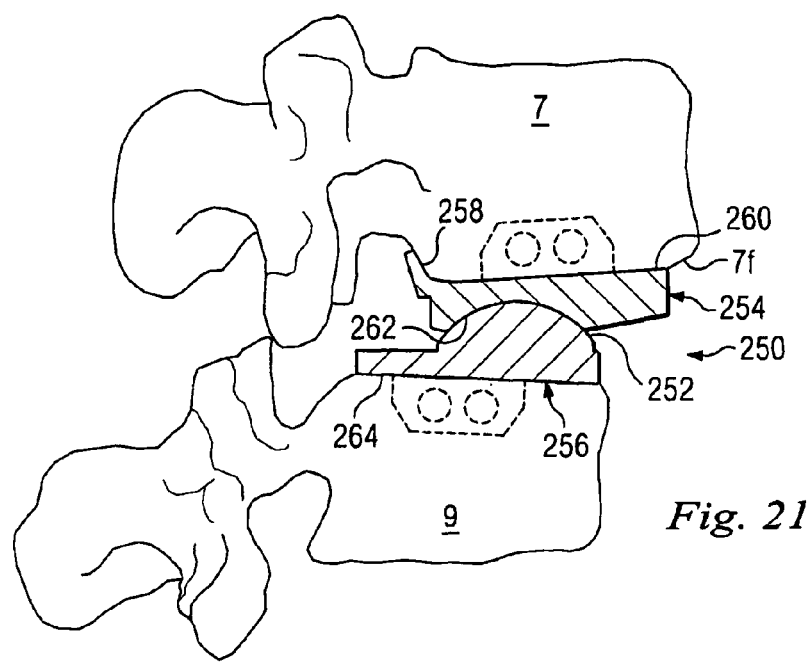
FIG. 21 is an exploded perspective view of another embodiment of the present disclosure.

Referring now to FIG. 21, in this embodiment, an artificial intervertebral joint 250 may include a spacer 252 interposed between two endplate assemblies 254, 256. U.S. application Ser. No. 10/042,589 entitled "Intervertebral Prosthetic Joint," filed Jan. 9, 2002 and U.S. application Ser. No. 10/752,860 entitled "Mobile Bearing Articulating Disc," filed Jan. 7, 2004 are incorporated by reference herein and disclose an intervertebral joint similar to intervertebral joint 250. Intervertebral joint 250, however, may include one or more additional support tabs 258 to reduce or prevent the formation of subsidence patterns in the vertebra 7. In this embodiment, the endplate assembly 254 may include an exterior surface 260 and a superior retaining portion 262. In this embodiment, the spacer 252 may be integrally formed with the endplate assembly 256 which may include an inferior exterior surface 264. The retaining portion 262 may be a recess that matches the shape of and permits smooth articulation with the spacer 102.

In this embodiment, the joint 250 may be installed between the vertebral bodies 7, 9 using an anterior approach. The spacer 252 may be placed into articulating contact with the superior retaining portion 262. In this embodiment, the exterior surface 260 may not extend to the posterior edge of the endplate 7*f*, so to prevent subsidence of this posterior edge, the support tab 258 may engage a portion of the endplate 7*f* between the exterior surface 260 and the posterior edge of the endplate 7*f*. The support tab 258 may further engage the posterior surface of the generally cylindrical body portion 7*a* of vertebra 7 to prevent subsidence of the vertebra 7. The additional surface area provided by the support tab or tabs 258 may dissipate forces over a greater surface area of the vertebra 7 and thus posterior subsidence patterns may be reduced. The support tabs may be configured to dodge neural structures, yet provide targeted bearing support on strong bone. The tab 258 may follow the natural contour of the body portion 7*a* and thus may form an angle other than ninety degrees with the bone contacting surface 260. In an alternative embodiment, one or more support tabs may extend from the inferior exterior surface to dissipate force over the vertebra 9 and reduce subsidence. Extending support tabs from the inferior exterior surface may, however, cause impingement upon neural structures. Thus, applying the support tabs in an asymmetrical manner with tabs on the superior component and omitted from the inferior component may protect nerve roots.

Figure 22:
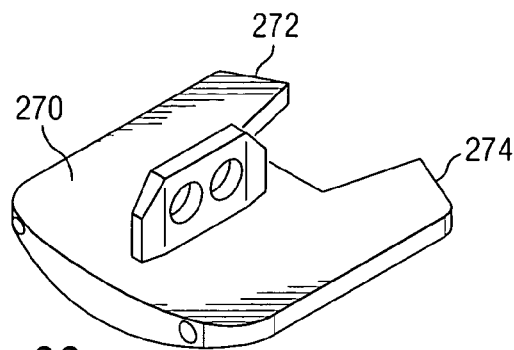
FIG. 22 is an exploded perspective view of another embodiment of the present disclosure.

Referring now to FIG. 22, an artificial intervertebral joint may include an endplate assembly 270 which may be substantially similar to the endplate assembly 254 except that support tabs 272, 274 may be relatively straight, engaging only the endplate 7*f* and omitting an angle or curve to engage the posterior surface of the generally cylindrical body portion 7*a*.

Figure 23:
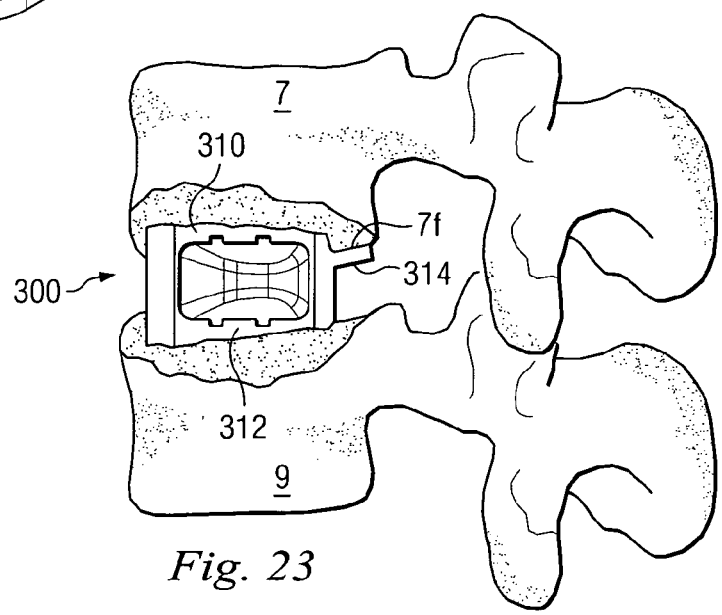
FIG. 23 is a cross-sectional view of another embodiment of the present disclosure.

Referring now to FIG. 23, a spinal implant may be a fusion cage 300 and may include a superior surface 310 and an inferior surface 312. The spinal implant may be substantially similar to the implant disclosed in U.S. Pat. No. 6,723,126 entitled, "Laterally Expandable Cage" filed Nov. 1, 2002 and incorporated by reference herein, except for the addition of a support tab 314. The support tab 314 may extend posteriorly from the superior surface 310 to engage the vertebral endplate 7*f*. The support tab 314 may prevent or limit subsidence of the endplate 7*f* that may otherwise result from even slight repeated movement of the superior surface 310 against the endplate 7*f*. It is understood that a support tab may be used with any spinal implant including cages for promoting fusing or motion preserving disc replacements.

Figure 24:
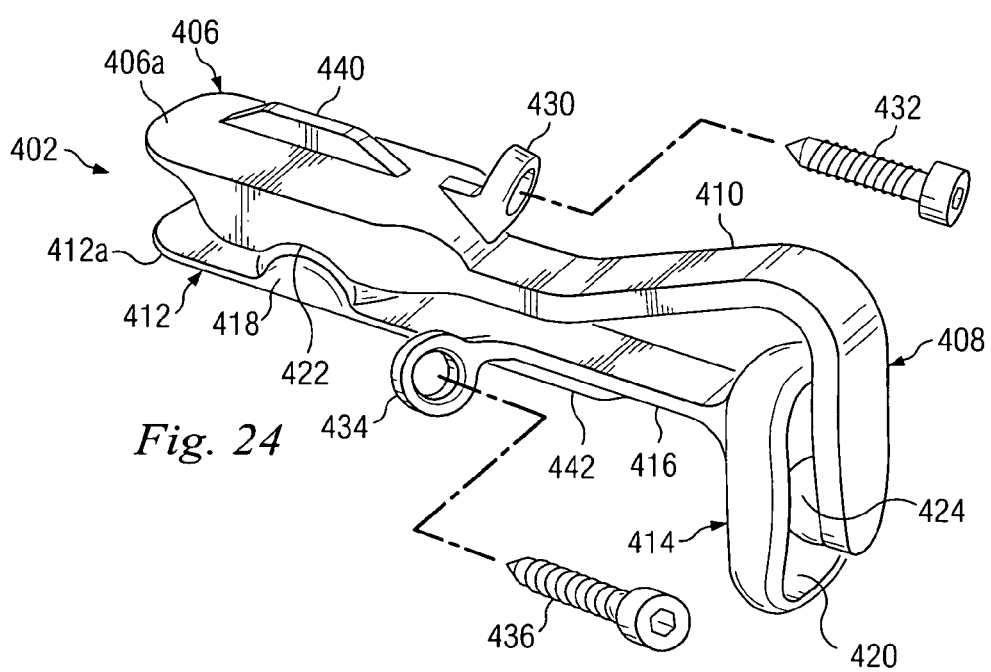
FIG. 24 is an assembled view of another embodiment of the present disclosure.

Referring now to FIG. 24, in this embodiment, one arthroplasty half 402 of an artificial intervertebral joint may be inserted between the vertebrae 7, 9. It is understood that a second arthroplasty half (not shown) may be inserted on an opposite lateral side, similar to the embodiments described above. The arthroplasty half 402 may include a rostral anterior joint component 406, a rostral posterior joint component 408, and a rostral bridge 410 extending between the anterior component 406 and the posterior component 408. The arthroplasty half 402 may further include a caudal anterior joint component 412, a caudal posterior joint component 414, and a caudal bridge 416 extending between the anterior component 412 and the posterior component 414. The rostral anterior joint component 406 may include a bone contacting surface 406a and the caudal anterior joint component 412 may include a bone contacting surface 412a.

Also in this embodiment, the caudal anterior joint component 412 may include a curved protrusion 418, and the caudal posterior joint component 414 may include a posterior socket 420. The rostral anterior joint component 406 may include an anterior socket 422 configured to receive the curved protrusion 418.

The rostral posterior joint component 408 may include a posterior protrusion 424 configured to engage the posterior socket 420. In this embodiment, the posterior protrusion may be a partial sphere that may rotate or translate within the socket 420, forming a loosely constrained The arthroplasty half 402 may further include features for affixing to the vertebrae 7, 9. It is understood, however, that in an alternative embodiment, the fixation features may be eliminated. Arthroplasty half 402 may include a connection component 430 extending rostrally from the rostral anterior joint component 406. The connection component 430 in this embodiment is a tab with an aperture adapted to receive a bone fastener such as screw 432. The orientation of the connection component 430 permits the screw 432 to affix to the cylindrical vertebral body 7a. In an alternative embodiment, the rostral connection component may permit connection with the pedicle of vertebra 7 as shown, for example, in FIG. 14. Arthroplasty half 402 may further include a connection component 434 attached to or integrally formed with the caudal anterior joint component 412. The connection component 434 in this embodiment is a tab with an aperture adapted to receive a bone fastener such as screw 436. The orientation of the connection component 434 permits the screw 436 to affix to the cylindrical vertebral body 9a. The connection components 430, 434 may also function as support tabs, providing additional surface area to dissipate forces and reduce subsidence.

The arthroplasty half 402 may further include a rostral keel 440 extending from the rostral anterior joint component 406 and a caudal keel 442 extending from the caudal anterior joint component 412 and down the caudal bridge 416. The keel 440 may allow the arthroplasty half 402 to engage the inferior endplate of the vertebral body 7a, and the keel 442 may allow the arthroplasty half 402 to engage the superior endplate of the vertebral body 9a and a superior face of a pedicle of vertebra 9. It is understood that the inferior endplate of the body 7a may be milled or otherwise prepared to receive the keel 440. Likewise, the superior endplate of the body 9a and the pedicle of vertebra 9 may be milled, chiseled, or otherwise prepared to create a channel for receiving the keel 442. The keels may help to connect to the bone and limit movement of the arthroplasty half 402 to the desired degrees to freedom. The keels may have an angled or semi-cylindrical cross section. It is understood that more than one keel may be used on any given component.

The arthroplasty half 402 may be installed similarly to the arthroplasty half 102 and may have similar motion in the anterior joint. In this embodiment, the ball shaped posterior protrusion 424 may be positioned in the socket 420 which is elongated to permit flexion-extension motion while limiting torsion. Locating the protrusion 424 on the rostral component 408, may simplify installation as the surgeon's view of the socket 420 and his/her ability to assemble the posterior joint may be improved.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. An artificial spinal joint for creating a portion of a coupling between a superior vertebra and an inferior vertebra comprising:
    an anterior joint replacement component comprising a ball and socket joint and a laterally facing outer surface, the ball and socket joint comprising a socket having an open lateral side portion flush with the laterally facing outer surface and comprising a curved protrusion having a lateral sidewall forming a part of the laterally facing outer surface, a radius of curvature of the curved protrusion closely matching a radius of curvature of the socket;
    a bridge coupled to the anterior joint replacement and extending posteriorly from the anterior joint replacement beyond one or both generally cylindrical body portions of a superior vertebra and an inferior vertebra;
    a posterior joint replacement component coupled to the bridge, wherein the posterior joint replacement component includes a rostral component and a caudal component, and wherein one of the rostral component and the caudal component is arranged to extend further posteriorly than the other one of the rostral component and the caudal component; and
    a support tab coupled to the anterior joint replacement component and arranged to engage a posterior surface of the generally cylindrical body portion of the superior vertebra.

2. The artificial spinal joint of claim 1 further comprising a fastener configured in a manner to fasten the support tab to the generally cylindrical body portion of the superior vertebra.

3. The artificial spinal joint of claim 2 wherein the fastener is a bone screw.

4. The artificial spinal joint of claim 2 wherein the fastener includes a plurality of bone screws.

5. The artificial spinal joint of claim 1 wherein the support tab is shaped to follow the contour of the posterior surface of the generally cylindrical body portion of the superior vertebra.

6. The artificial spinal joint of claim 5 wherein an angle between the support tab and the anterior joint replacement component is greater than 90 degrees.

7. The artificial spinal joint of claim 1 wherein the support tab is rigidly coupled to the anterior joint replacement component.

8. The artificial spinal joint of claim 1 wherein a surface of the support tab is coated with osteoconductive material.

9. The artificial spinal joint of claim 1 wherein a surface of the support tab is roughened in a manner to promote bone ingrowth.

10. The artificial spinal joint of claim 1 wherein the bridge is at least a portion of an artificial pedicle.

11. An artificial spinal joint replacement device for placement between a superior vertebra and an inferior vertebra, the device comprising:

an upper retaining portion; and a lower retaining portion, the upper and lower retaining portions each having an anterior joint replacement element sized to fit within a space between vertebral bodies of the superior and inferior endplates, the anterior joint replacement elements together forming a ball and socket joint and having a laterally facing outer surface, the ball and socket joint comprising a socket having an open lateral side portion flush with the laterally facing outer surface and comprising a curved protrusion having a lateral sidewall forming a part of the laterally facing outer surface, a radius of curvature of the curved protrusion closely matching a radius of curvature of the socket;

at least one of the upper and lower retaining portions having a posterior element connected to the anterior joint replacement element, such that an overall length of said at least one of the upper and lower retaining portions is greater than an overall length of the other of the upper and lower retaining portions, said at least one of the upper and lower retaining portions being sized so that the posterior element is disposed outside the space between the vertebral bodies when the anterior joint replacement element is disposed within the space between the vertebral bodies, wherein the posterior element includes a connector hole configured to receive a fastener to secure said at least one of the upper and lower retaining portions to the respective superior or inferior vertebrae.

12. The joint replacement device of claim 11, further comprising a bridge section extending between and connecting the posterior element and the anterior joint replacement element of said at least one of the upper and lower retaining portions.

13. The joint replacement device of claim 11, wherein the connector hole is disposed in a manner that directs the fastener into a pedicle of the respective superior and inferior vertebrae.

14. The joint replacement device of claim 11, wherein the upper retaining portion is shaped in a manner that allows it to directly contact only the upper vertebra and the lower retaining portion is shaped in a manner that allows it to directly contact only the lower vertebra.

15. The joint replacement device of claim 11, wherein the upper and lower retaining portions are shaped for implantation on one side of a midline of the superior and inferior vertebrae.

16. The joint replacement device of claim 11, comprising:

a second upper retaining portion; and a second lower retaining portion, the second upper and second lower retaining portions each having a second anterior joint replacement element sized to fit within a space between vertebral bodies of the superior and inferior endplates, the second upper and lower retaining portions being sized for implantation on one side of a midline of the superior and inferior vertebrae.

17. The joint replacement device of claim 11, wherein said at least one of the upper and lower retaining portions having a posterior element is the lower retaining portion.

18. The joint replacement device of claim 11, wherein the upper and lower retaining portions are sized for implantation though a posterior approach.

19. The joint replacement device of claim 11, wherein the upper and lower retaining portions are sized for implantation through a posterior approach without requiring removal of facet joints.

20. An artificial spinal joint replacement device for placement between a superior vertebra and an inferior vertebra, the device comprising:

an upper retaining portion including an upper endplate contact surface configured in a manner to contact an endplate of the superior vertebra, a lower surface; and a lower retaining portion including a lower endplate contact surface configured in a manner to contact an endplate of the inferior vertebra, an upper surface facing the lower surface of the upper retaining portion, the upper and lower retaining portions each having an anterior joint replacement element sized to fit within a space between vertebral bodies of the superior and inferior endplates and shaped in a manner that cooperatively provides movement of the upper retaining portion relative to the lower retaining portion in a manner to provide relative movement to the superior and inferior vertebra, the upper and lower retaining portions comprising a ball and socket joint and having a laterally facing outer surface, the ball and socket joint comprising a socket having an open lateral side portion flush with the laterally facing outer surface and comprising a curved protrusion having a lateral sidewall forming a part of the laterally facing outer surface, a radius of curvature of the curved protrusion closely matching a radius of curvature of the socket;

at least one of the upper and lower retaining portions having a posterior element connected to the anterior joint replacement element, such that an overall length of said at least one of the upper and lower retaining portions is greater than an overall length of the other of the upper and lower retaining portions, said at least one of the upper and lower retaining portions being sized so that the posterior element is disposed outside the space between the vertebral bodies when the anterior joint replacement element is disposed within the space between the vertebral bodies, wherein the posterior element includes a connector hole configured to receive a fastener to secure said at least one of the upper and lower retaining portions to the respective superior or inferior vertebrae.

21. The joint replacement device of claim 20, further comprising a bridge section extending between and connecting the posterior element and the anterior joint replacement element of said at least one of the upper and lower retaining portions.

22. The joint replacement device of claim 20, wherein the connector hole is disposed in a manner that directs the fastener into a pedicle of the respective superior and inferior vertebrae.

23. The joint replacement device of claim 20, comprising:

a second upper retaining portion; and a second lower retaining portion, the second upper and second lower retaining portions each having a second anterior joint replacement element sized to fit within a space between vertebral bodies of the superior and inferior endplates, the second upper and lower retaining portions being sized for implantation on one side of a midline of the superior and inferior vertebrae.

* * * * *